United States Patent [19]

Rosen

[11] 4,242,266
[45] Dec. 30, 1980

[54] 1-BENZOTHIEPIN-4-CARBOXYLIC ACID DERIVATIVES

[75] Inventor: Melvin H. Rosen, Madison, N.J.

[73] Assignee: Ciba-Geigy Corporation, Ardsley, N.Y.

[21] Appl. No.: 937,633

[22] Filed: Aug. 29, 1978

Related U.S. Application Data

[60] Division of Ser. No. 763,192, Jan. 27, 1977, Pat. No. 4,166,126, which is a continuation of Ser. No. 585,147, Jun. 9, 1975, abandoned, which is a continuation-in-part of Ser. No. 509,524, Sep. 26, 1974, abandoned.

[51] Int. Cl.³ .................. C07D 409/04; C07D 337/08
[52] U.S. Cl. .......................... 260/326.34; 260/326.25; 260/326.5 SA; 544/145; 544/238; 544/336; 546/202; 548/215; 548/240; 548/336; 548/374; 548/200; 548/206; 549/9
[58] Field of Search ................ 260/326.34, 326.5 SA, 260/327 B; 546/202; 549/9

[56] References Cited

U.S. PATENT DOCUMENTS

| | | | |
|---|---|---|---|
| 3,287,368 | 11/1966 | Mohrbacher et al. | 260/327 B |
| 3,287,370 | 11/1966 | Mohrbacher et al. | 260/327 B |
| 3,389,144 | 6/1968 | Mohrbacher et al. | 260/327 B |
| 3,444,176 | 5/1969 | Mohrbacher | 260/327 B |
| 3,505,355 | 4/1970 | Mohrbacher et al. | 260/327 B |
| 3,551,455 | 12/1970 | Mohrbacher et al. | 260/327 B |
| 3,826,791 | 7/1974 | Zinnes et al. | 260/327 B |
| 3,828,055 | 8/1974 | Zinnes et al. | 260/327 B |
| 3,962,261 | 6/1976 | Zinnes et al. | 260/327 B |
| 4,046,778 | 9/1977 | Zinnes et al. | 260/327 B |
| 4,166,126 | 8/1979 | Rosen | 260/326.34 |
| 4,185,109 | 1/1980 | Rosen | 260/326.34 |

FOREIGN PATENT DOCUMENTS

| | | | |
|---|---|---|---|
| 2145691 | 2/1973 | France | 260/327 B |
| 2183008 | 12/1973 | France | 260/327 B |

OTHER PUBLICATIONS

Sindelar et al., Coll. Czech. Chem. Commun., vol. 37, pp. 1195–1206 (1972).

Primary Examiner—Mary C. Lee
Attorney, Agent, or Firm—Theodore O. Greoger

[57] ABSTRACT

2,3-Dihydro-1-benzothiepin-4-carboxamides, e.g. those of the formula

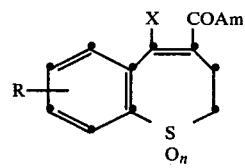

Am = NH$_2$, mono- or di-(alkyl or HO-alkyl)-amino, alkyleneimino, cycloalkylamino, iso- or heterocyclic arylamino or N-alkyl-N-arylamino
X = HO, alkoxy, alkanoyloxy or tert.Am
R = H, alkyl, alkoxy, alkylmercapto, halo, CF$_3$, CN or NO$_2$
n = 0-2 or their salts with therapeutically useful bases, exhibit anti-inflammatory effects.

2 Claims, No Drawings

1-BENZOTHIEPIN-4-CARBOXYLIC ACID DERIVATIVES

CROSS-REFERENCE TO RELATED APPLICATION

This is a divisional of application Ser. No. 763,192, filed on Jan. 27, 1977, now U.S. Pat. No. 4,166,126, which in turn is a continuation of application Ser. No. 585,147, filed June 9, 1975 (now abandoned), which in turn is a continuation-in-part of application Ser. No. 509,524, filed Sept. 26, 1974 (now abandoned).

SUMMARY OF THE INVENTION

The present invention concerns and has for its object the provision of new 2,3-dihydro-1-benzothiepin-4-carboxamides, preferably of those corresponding to Formula I

wherein Ph is 1,2-phenylene optionally substituted by one or more members selected from lower alkyl, lower alkoxy, lower alkylmercapto, halogeno, trifluoromethyl, cyano or nitro, X is hydroxy, lower alkoxy, lower alkanoyloxy, di-lower alkylamino or lower alkyleneimino, Am is amino, mono- or di-(lower alkyl or hydroxyalkyl)amino, lower alkyleneimino, lower mono- aza, oxa or thia- alkyleneimino, cycloalkylamino, H-Ph-amino, N-lower alkyl-H-Ph-amino, Hc-amino or N-lower alkyl-Hc-amino, wherein Hc is heterocyclic aryl selected from furyl, thienyl, pyrryl, 1,2- or 1,3-oxazolyl or -thiazolyl, pyrazolyl, imidazolyl, pyridyl, pyridazinyl, pyrimidyl or pyrazinyl, or the lower alkylated derivatives thereof, "alk" is lower alkylene separating the adjacent sulfur from the quaternary carbon atom by two carbon atoms and n is an integer from 0 to 2, or a salt thereof derived from a therapeutically useful base; as well as of corresponding pharmaceutical compositions and of methods for the preparation and application of these products, which are useful antiinflammatory agents.

DESCRIPTION OF THE PREFERRED EMBODIMENTS

The 1,2-phenylene radical Ph is unsubstituted or substituted by one or more than one, preferably by one or two, of the same or different members selected from the group consisting of lower alkyl, e.g. methyl, ethyl, n- or i-propyl or -butyl; etherified or esterified hydroxy or mercapto, such as lower alkoxy, e.g. methoxy, ethoxy, n- or i-propoxy or -butoxy; methyl- or ethylmercapto; or halogeno, e.g. fluoro, chloro or bromo; trifluoromethyl, cyano or nitro. The term "lower", referred to above and hereinafter in connection with organic radicals or compounds respectively, defines such with up to 7, preferably up to 4, carbon atoms. Preferred 1,2-phenylene radicals Ph are 1,2-phenylene, (lower alkyl)-1,2-phenylene, (lower alkoxy)-1,2-phenylene, (lower alkylmercapto)-1,2-phenylene, mono- or di-(halogeno)-1.2-phenylene or (tri-fluoromethyl)-1,2-phenylene.

In case X is hydroxy, the compounds of the invention are depicted by Formula I as the tautomeric enols (derived from the corresponding 5-ketones), rendering them acidic to form salts with said bases. In case X is lower alkoxy, or alkanoyloxy, e.g. acetoxy, propionyloxy or pivalyloxy, said formula depicts enolethers or -esters, and in case X is said tert. amino, the formula depicts enamines, which are no longer acidic.

The amino group Am and said tert. amino group X are examplified by amino, mono- or di-(lower alkyl or hydroxyalkyl)-amino. e.g. mono- or di-(methyl, ethyl, n- or i-propyl or -butyl; 2-hydroxyethyl or 2- or 3-hydroxypropyl)-amino; lower alkylene imino, e.g. pyrrolidino, piperidino, 1,4-, 1,5-, 1,6-, 2,5, - 2,6- or 1,7-hexylene or -heptyleneimino; lower mono-aza, -oxa or -thiaalkyleneimino, e.g. piperazino, homopiperazino, morpholino or thiamorpholino. Cycloalkylamino is preferably 3 to 7 ring-membered, e.g. cyclopropylamino, cyclopentylamino or cyclohexylamino and the (H-Ph or Hc) amino or N-lower alkyl-N-(H-Ph or Hc)-amino groups are illustrated by (phenyl, tolyl, anisyl, methylmercaptophenyl, mono- or di-fluoro or -chlorophenyl, bromophenyl, trifluoromethylphenyl, cyanophenyl or nitrophenyl; 2- or 3-furyl, -thienyl or -pyrryl, 5-methyl-3-1,2-oxazolyl or -thiazolyl, 2-1,3-oxazolyl or -thiazolyl, 3-pyrazolyl, 2-imidazolyl, 2-, 3- or 4-pyridyl, 4-pyridazinyl, 2-pyrimidyl or 2-pyrazinyl)-amino, or the N-methylated tert. amino and/or ring-methylated analogs thereof.

The lower alkylene group "alk" represents preferably 1,2-ethylene, but also 1,2-propylene, 1,2- or 2,3-butylene, 1,2- or 2,3-pentylene.

Therapeutically useful bases for the formation of salts with said enols (X=OH) are preferably alkali metal hydroxides, ammonia or amines illustrated by H-Am or lower alkyl-Am, e.g. sodium, potassium, ammonium, mono-, di- or trimethyl- or -ethyl-ammonium, pyrrolidinium, morpholinium, anilinium or 2-pyridyl-ammonium salts.

The compounds of the invention exhibit valuable pharmacological properties, primarily anti-inflammatory activity. This can be demonstrated by in-vitro or in-vivo tests, using for the latter advantageously mammals, such as rats or dogs, as test objects. The compounds of the invention can be administered to the animals either enterally, preferably orally, parenterally, e.g. subcutaneously or intravenously, or topically, for example in the form of aqueous or oily solutions or starchy suspensions. The applied dosage may range between about 0.1 and 200 mg/kg/day. preferably between about 1 and 100 mg/kg/day, advantageously between about 5 and 50 mg/kg/day. The tests chosen are among the classical assay methods for said activity, such as the carrageenin paw-edema or adjuvant arthritis test in rats, or more recent tests described by Perper et al. in Arthritis Rheum. 17, 47 (1974). There $^{35}$S-labelled rabbit ear cartilage degradation is induced by the non-phagocytic release of neutral proteases from viable human leukocytes. Anti-rheumatic agents prevent this enzyme-release at concentrations correlated with their blood levels usually achieved in man. In addition, the compounds of the invention inhibit the neutral proteases themselves.

Thus, for example, the N-(4-fluorophenyl,2,4- or 3,4-dichlorophenyl)-7-chloro-5-(hydroxy or pyrrolidino)-2,3-dihydro-1-benzothiepin-1,1-dioxide-4-carboxamides, representative members of the compounds of Formula I, are highly active in rats at p.o. doses as low as 1 mg/kg/day in the paw-edema and adjuvant arthritis essay and prevent at very low concentrations the $^{35}$S-enzyme-release from viable human leukocytes in vitro. Accordingly, the compounds of the invention are useful antiinflammatory agents, for example in the treatment or management of arthritic and dermatopathologic conditions.

Particularly useful are compounds of Formula I, wherein Ph is 1,2-phenylene, unsubstituted or substituted by one or two of the same or different members selected from lower alkyl, lower alkoxy, lower alkylmercapto, halogeno, trifluoromethyl, cyano or nitro, X is hydroxy, lower alkoxy, lower alkanoyloxy, di-lower alkylamino or lower alkyleneimino, Am is amino, mono- or di-(lower alkyl or hydroxyalkyl)-amino, lower alkyleneimino, piperazino, 4-lower alkylpiperazino, morpholino, thiamorpholino, 3 to 7 ring-membered cycloalkylamino, H-Ph-amino, N-lower alkyl-H-Ph-amino, Hc-amino or N-lower alkyl-Hc-amino, wherein Hc is heterocyclic aryl selected from furyl, thienyl, pyrryl, 1,2- or 1,3-oxazolyl or -thiazolyl, pyrazolyl, imidazolyl, pyridyl, pyridazinyl, pyrimidyl or pyrazinyl, or the lower alkylated derivatives thereof, "alk" is lower alkylene separating the adjacent sulfur from the quaternary carbon atom by two carbon atoms and n is an integer from 0 to 2, or a salt thereof derived from a therapeutically useful base.

Preferred compounds of the invention are those of Formula I, wherein Ph is 1,2-phenylene, (lower alkyl)-1,2-phenylene, (lower alkoxy)-1,2-phenylene, (lower alkylmercapto)-1,2-phenylene, mono- or di-(halogeno)-1,2-phenylene or (trifluoromethyl)-1,2-phenylene. sX is hydroxy, lower alkanoyloxy or 5 to 7 ring-membered lower alkyleneimino, Am is mono- or di-lower alkylamino, 5 to 7 ring-membered lower alkyleneimino, 5 to 7 ring-membered cycloalkylamino H-Ph-amino or Hc-amino, wherein Hc is 2- or 3-furyl, -thienyl or -pyrryl, 5-methyl-3-1,2-oxazolyl or -thiazolyl, 2-1,3-oxazolyl or -thiazolyl, 3-pyrazolyl, 2-imidazolyl, 2-, 3- or 4-pyridyl, 4-pyridazinyl, 2-pyrimidyl or 2-pyrazinyl, or the ring-monomethylated derivatives thereof, "alk" is 1,2-ethylene or 1,2-propylene and n is an integer from 0 to 2, or a salt thereof derived from a therapeutically useful base.

Outstanding are compounds of Formula II

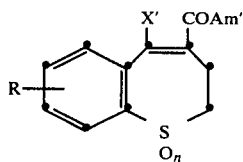

(II)

wherein R is methyl, t. butyl, methoxy, methylmercapto, fluoro, chloro, bromo or trifluoromethyl, X' is hydroxy, acetoxy, pyrrolidino or piperidino, Am' is (phenyl, tolyl, anisyl, methylmercaptophenyl, mono- or di-fluoro or -chlorophenyl, bromophenyl, trifluoromethylphenyl, 5-methyl-3-1,2-oxazolyl or -thiazolyl, 2-1,3-oxazolyl or -thiazolyl, 3-pyrazolyl, 2-imidazolyl, 2-,3- or 4-pyridyl)-amino, and n is an integer from 0 to 2 or the sodium, potassium, ammonium, mono-, di- or trimethyl- or -ethylammonium, pyrrolidinium, morpholinium or H-Am salt thereof.

Especially valuable are those compounds of Formula II, wherein R is chlorine in the 7-position, X is hydroxy or pyrrolidino, Am is mono- or di-fluoro or -chlorophenylamino and n is an integer from 0 to 2, or the sodium, potassium, ammonium, mono-, di- or trimethyl- or -ethylammonium, pyrrolidinium, morpholinium, anilinium or 2-pyridylammonium salt thereof.

The compounds of the invention are prepared according to conventional methods, for example by (a) reacting a corresponding 2,3-dihydro-1-benzothiepin-4-carboxylic acid ester, anhydride or halide of Formula III

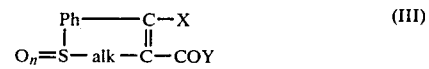

(III)

wherein Y is lower alkoxy, alkanoyloxy or halogeno, with the amine H-Am or (b) adding to a corresponding 4-unsubstituted 2,3-dihydro-1-benzothiepin of Formula IV

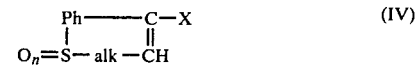

(IV)

the isocyanate Am"=CO, wherein Am" is a primary or secondary amino group selected from Am and, if desired, converting any resulting product into another compound of the invention.

The amination according to item (a) is carried out in the usual manner, advantageously between about room temperature and about 200°, either with equivalent amounts of the reactants, preferably when the ester is used, or with an excess of the amine or the presence of another base, such as a tertiary amine, e.g. a tri-lower alkylamine or pyridine, when the halide or anhydride is used, in order to neutralize the generated acid. The lower alkanol, generated in the reaction with said esters, is preferably distilled off together with diluent, such as an aromatic hydrocarbon, e.g. benzene, toluene or xylene.

The addition of the isocyanate according to item (b) is preferably carried out with compounds of Formula III wherein X is either hydroxy, or an alkali metal salt thereof, or wherein X is advantageously said tert. amino, and an equivalent amount or slight excess of the isocyanate, preferably between about room temperature and about 100° and the presence of a polar solvent, such as an ether, e.g. diethyl ether or tetrahydrofuran.

The compounds of Formula I, so obtained, can be converted into each other according to methods known per se. Thus, for example, the enols (X=OH) can be obtained from the enol ethers (X=alkoxy) or preferably the enamines (X=di-lower alkylamino or lower alkyleneimino) by acidic hydrolysis, advantageously with the use of hydrohalic acids. The resulting enols can be salified with said therapeutically useful bases or alkali metal hydrides, advantageously in the presence of an alcoholic solvent, such as a lower alkanol, e.g. ethanol, or an ether, e.g. tetrahydrofuran, or an amide, e.g. dimethylformamide, at moderate temperatures, e.g. below 100°. Resulting salts may also be acylated, for example with lower alkanoyl halides, e.g. acetyl chloride, to yield said enol esters. In case said enols are reacted with di-lower alkylamines or lower alkyleneimines at rised temperatures and for a longer period of time, the enamines of Formula I are obtained. Said enols with n=0 can also be oxidized to the corresponding 1-oxides or 1,1-dioxides with the use of mild or strong oxidants, such as periodates, e.g. sodium periodate in said polar solvents and at low temperatures, e.g. between about 0° and room temperature for the former, or hydrogen peroxide or organic peracids, such as lower peralkanoic or perbenzoic acids, e.g. peracetic or m-chloroperbenzoic acid, advantageously at temperatures at or below room temperature with the latter, or up to 100° with diluted hydrogen peroxide in the presence of lower alkanoic acids, e.g. acetic acid. Care should be taken, especially with said peracids, in order to prevent overoxidation at overly long reaction times, yielding compounds of Formula V

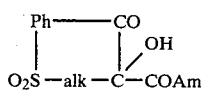

with similar pharmacological effects as those of Formula I.

The starting materials used are known or, if new, can be prepared according to the methods used for the known analogs or illustrated by the examples herein. Thus, esters of Formula III are described in Collection Czechoslov. Chem. Commun. Vol. 37. p. 1195 (1972) and compounds of Formula IV in J. Org. Chem. 26, 2728 (1961) or J. Chem. Soc. (c), 1971, p. 2252. The latter enamines may also be reacted with phosgenes, to yield the acid halides of Formula III, and these with alkanoic acids to yield the anhydrides.

The above reactions are carried out according to standard methods, in the presence or absence of diluents, preferably such as are inert to the reagents and are solvents thereof, of catalysts, condensing or neutralizing agents and/or inert atmospheres, at low temperatures, room temperature or elevated temperatures, at atmospheric or superatmospheric pressure.

The invention also comprises any modification of the above process, wherein a compound resulting as an intermediate at any stage thereof, is used as starting material and the remaining steps are carried out, or the process is discontinued at any stage thereof, or in which the starting material is formed under the reaction conditions or is used in the form of its salts or reactive derivatives, preferably alkali metal salts of enols (X=OH). For example, isocyanates may be formed from the corresponding acid azides and mixed anhydrides from the acids corresponding to III and simple alkanoic acid anhydrides. In the process of the invention those starting materials are advantageously selected, which yield the above-described preferred embodiments of the invention, especially those corresponding to Formula II.

The pharmacologically active compounds of the invention are useful in the manufacture of pharmaceutical compositions containing an effective amount thereof in conjunction or admixture with excipients suitable for either enteral, parenteral or topical application. Preferred are tablets and gelatin capsules comprising the active ingredient together with (a) diluents, e.g. lactose, dextrose, sucrose, mannitol, sorbitol, cellulose and/or glycine, (b) lubricants, e.g. silica, talcum, stearic acid, its magnesium or calcium salt and/or polyethyleneglycol, for tablets also (c) binders, e.g. magnesium aluminum silicate, starch paste, gelatin, tragacanth, methylcellulose, sodium carboxymethylcellulose and/or polyvinylpyrrolidone, if desired (d) disintegrants, e.g. starches, agar, alginic acid or its sodium salt, enzymes of the binders or effervescent mixtures and/or (e) absorbents, colorants, flavors and sweeteners. Injectable compositions are preferably aqueous isotonic solutions or suspensions, and suppositories are advantageously made from fatty emulsions or suspensions. They may be sterilized and/or contain adjuvants, such as preserving, stabilizing, wetting or emulsifying agents, solution promoters, salts for regulating the osmotic pressure and/or buffers. Said pharmaceutical compositions may also contain other therapeutically valuable substances. They are prepared according to conventional mixing, granulating or coating methods respectively and contain about 0.1 to 75%, preferably about 1 to 50% of the active ingredient.

The following examples are intended to illustrate the invention and are not to be construed as being limitations thereon. Temperatures are given in degrees Centrigrade, all parts wherever given are parts by weight, and all evaporations are carried out under reduced pressure.

EXAMPLE 1

The stirred solution of 8.0 g of 7-chloro-5-hydroxy-2,3-dihydro-1-benzothiepin-1,1-dioxide-4-carboxylic acid methyl ester. 2.5 G of 2-aminopyridine and 160 ml of dry toluene is refluxed for 6 hours, while 30 ml of the solvent is distilled off and replaced by the same amount of toluene. After about 5 hours the mixture is cooled, filtered, and the solid washed with toluene. It is heated with 50 ml of ethanol, the mixture filtered while hot and the residue collected, to yield the N-2=-pyridylamino-7-chloro-5-hydroxy-2,3-dihydro-1-benzothiepin-1,1-dioxide-4-carboxamide of the formula

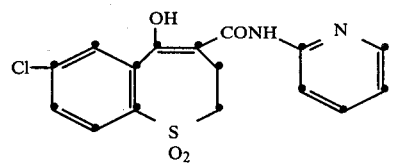

melting at 211°–213°.

The ethanolic filtrate is evaporated and the residue recrystallized from ethanol to yield a small amount of the 2-pyridylammonium salt of said amide melting at 171°–174°.

The starting material is prepared as follows: The mixture of 31.0 g of 7-chloro-5-hydroxy-2,3-dihydro-1-benzothiepin (Brit. Patent 1,112,681) 126 ml of acetic acid and 77.7 ml of 30% aqueous hydrogen peroxide is left at room temperature for overnight, swirled, then heated on a steam bath for 1 hour. The mixture is cooled, swirled, and poured into 600 ml of ice-water. It is filtered, the solid rinsed with 1000 ml of water and dried, to yield the 7-chloro-5-hydroxy-2,3-dihydro-1-benzothiepin-1,1-dioxide melting at 166°–168°.

The mixture of 9.4 g thereof, 4.0 g of pyrrolidine, 0.01 g of p-toluenesulfonic acid, and 100 ml of dry benzene is refluxed for 4 days on a water trap until the theoretical amount of water is collected. Thereupon it is evaporated, to yield the 7-chloro-5-pyrrolidino-2,3-dihydro-1-benzothiepin-1,1-dioxide about 90% pure. (The analogously prepared 7-unsubstituted compound boils at 190°/0.15 mmHg. whereas the 7-chloro-5-piperidino-analog melts at 108°–112°.)

The solution of 26.8 g thereof in 360 ml of dry tetrahydrofuran and 14.8 ml of triethylamine is added during 35 minutes to the mixture of 86.4 ml of 12.5% phosgene in benzene and 54 ml of dry tetrahydrofuran while stirring at −15°. The mixture is allowed to warm to room temperature and stirred for 3 hours, to yield a solution of 7-chloro-5-pyrrolidino-2,3-dihydro-1-benzothiepin-1,1-dioxide-4-carboxylic acid chloride useful for the amination according to (a).

It is treated with the solution of 14.8 ml of triethylamine and 210 ml of methanol during 10 minutes, whereby the temperature rises to 34°. The mixture is stirred at room temperature for 1 hour, refluxed for 13 hours and concentrated to one-half its volume. The concentrate is diluted with 360 ml of water, extracted with chloroform, the extract washed with water, dried and evaporated, to yield the 7-chloro-5-pyrrolidino-2,3-dihydro-1-benzothiepin-1,1-dioxide-4-carboxylic acid methyl ester.

The mixture of 32.0 g thereof, 30 ml of 6N aqueous hydrochloric acid and 300 ml of methanol is refluxed for 1.25 hours and the precipitate collected after cooling, to yield the 7-chloro-5-hydroxy-2,3-dihydro-1-benzothiepin-1,1-dioxide-4-carboxylic acid methyl ester melting at 150°–152° (The analogously prepared 7-unsubstituted ester melts at 140°–143°).

EXAMPLE 2

To the solution of 6.0 g of 7-chloro-5-pyrrolidino-2,3-dihydro-1-benzothiepin-1,1-dioxide in 6 ml of dry tetrahydrofuran that of 2.8 g of p-fluorophenylisocyanate in 6 ml of tetrahydrofuran is added dropwise while stirring under nitrogen. The mixture is held at 40°–45° for one hour at room temperature for one hour and then cooled to 0° with an ice-bath. It is filtered, the solid rinsed with cold tetrahydrofuran, triturated with cold diethyl ether and recrystallized from acetonitrile or ethyl acetate, yielding N-p-fluorophenyl-7-chloro-5-pyrrolidino-2,3-dihydro-1-benzothiepin-1,1-dioxide-4-carboxamide of the formula

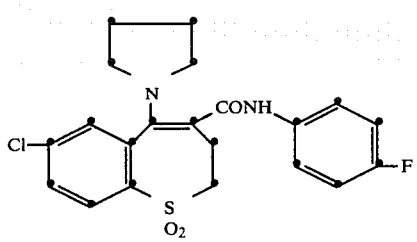

melting at 163°–165°.

EXAMPLE 3

The mixture of 6.0 g of N-p-fluorophenyl-7-chloro-5-pyrrolidino-2,3-dihydro-1-benzothiepin-1,1-dioxide-4-carboxamide and 60 ml of ethanol is treated at room temperature with 6.0 ml of 6N hydrochloric acid in one portion while stirring. It is refluxed for one hour and left overnight at room temperature. It is cooled in an ice-bath and the precipitate collected, to yield the N-p-fluorophenyl-7-chloro-5-hydroxy-2,3-dihydro-1-benzothiepin-1,1-dioxide- 4-carboxamide melting at 167°–169°.

The mixture of 3.5 g thereof and 20 ml ethanol is treated with 3 ml of pyrrolidine in one portion. A reaction is evidenced by a color change from colorless to yellow and the formation of a homogeneous solution. The mixture is refluxed for two minutes, cooled, treated with 10 ml of diethyl ether, the precipitate formed filtered off and rinsed with diethyl ether to yield the corresponding pyrrolidinium salt melting at 175°–177°. The analogously prepared morpholinium salt melts at 193° to 196°.

EXAMPLE 4

According to the method shown in Example 2, the N-p-fluorophenyl-7-chloro-5-pyrrolidino-2,3-dihydro-1-benzothiepin-1-oxide-4-carboxamide is prepared from equivalent amounts of the corresponding reagents, it melts at 189°–190°.

It can be hydrolyzed as shown in Example 3, to yield the N-p-fluorophenyl-7-chloro-5-hydroxy-2,3-dihydro-1-benzothiepin-1-oxide-4-carboxamide, melting at 218°–219° with decomposition.

The starting material is prepared as follows: The solution of 6.4 g of 7-chloro-5-hydroxy-2,3-dihydro-1-benzothiepin in 65 ml of dry methanol and 65 ml of dry dioxane is treated dropwise at 0° in 1 hour with the solution of 7.0 g of sodium metaperiodate in 65 ml water. The mixture is stirred at 0° for two hours after the addition period and then allowed to warm to room temperature for overnight. It is filtered and the solid rinsed with 30 ml of methanol. The combined filtrate and wash is concentrated to a smaller volume and treated with 40 ml of water. The mixture is extracted with chloroform, the extract separated, washed with water, dried and evaporated, to yield the 7-chloro-5-hydroxy-2,3-dihydro-1-benzothiepin-1-oxide boiling at 154–157/0.25 mmHg.

It is converted into the 7-chloro-5-pyrrolidino-2,3-dihydro-1-benzothiepin-1-oxide as described in Example 1.

EXAMPLE 5

According to the methods illustrated by the previous examples (indicated in the table below), the following compounds of Formula II are prepared from equivalent amounts of the corresponding reagents: Am=NH-Z, R is in 7-position; Pyr=pyrrolidino, Pip=piperidino; c=xylene as solvent

| No. | Ex. | Z | X | R | n | m.p. °C. | recryst. from |
|---|---|---|---|---|---|---|---|
| 1 | 1c | 2-thiazolyl | OH | H | 0 | 205–208 | benzene |
| 2 | 1 | " | " | H | 2 | 252–254 | — |
| 3 | 1c | " | " | Cl | 0 | 211–213 | acetone |
| 4 | 1 | " | " | Cl | 2 | 230–231 | — |
| 5 | 1 | 5-CH₃—3-isoxazolyl | " | Cl | 2 | 210–212 | — |
| 6 | 1 | 2,4-F₂—C₆H₃ | " | Cl | 2 | 201–203 | — |
| 7 | 2 | n-butyl | Pyr | Cl | 2 | 149–151 | — |
| 8 | 2 | cyclohexyl | " | Cl | 2 | 165–167 | CH₃CN |
| 9 | 2 | phenyl | " | H | 0 | 125–128 | — |
| 10 | 2 | 4-F—C₆H₄ | " | Cl | 0 | 149–150 | — |
| 11 | 2 | 4-CH₃O—C₆H₄ | " | Cl | 2 | 147–149 | CH₃CN |
| 12 | 2 | 4-CH₃S—C₆H₄ | " | Cl | 2 | 162–164 | — |
| 13 | 2 | 2-F—C₆H₄ | " | Cl | 2 | 160–162 | — |
| 14 | 2 | 4-F—C₆H₄ | Pip | Cl | 2 | 168–171 | — |
| 15 | 2 | " | Pyr | H | 0 | 145–147 | ethanol |
| 16 | 2 | 4-Cl—C₆H₄ | " | H | 2 | 134–137 | " |
| 17 | 2 | " | " | H | 0 | 106–108 | benzene |
| 18 | 2 | 4-Br—C₆H₄ | " | H | 0 | 109–112 | — |
| 19 | 2 | 2-CF₃—C₆H₄ | " | H | 0 | 115–116 | ethanol |
| 20 | 2 | 2,5-F₂—C₆H₄ | " | Cl | 2 | 153–155 | — |
| 21 | 2 | 3-Cl—4-F—C₆H₃ | " | Cl | 2 | 136–138 | CH₃CN |
| 22 | 3 | phenyl | OH | H | 0 | 165–167 | — |
| 23 | 3 | 4-CH₃S—C₆H₄ | " | Cl | 2 | 205–207 | — |
| 24 | 3 | 2-F—C₆H₄ | " | Cl | 2 | 141–143 | — |
| 25 | 3 | 4-F—C₆H₄ | " | H | 0 | 202–204 | — |
| 26 | 3 | " | " | Cl | 0 | 160–163 | — |
| 27 | 3 | " | " | H | 2 | 193–195 | ethanol |
| 28 | 3 | 4-Cl—C₆H₄ | " | H | 0 | 196–198 | — |
| 29 | 3 | 4-Br—C₆H₄ | " | H | 0 | 200–201 | — |
| 30 | 3 | 2-CF₃—C₆H₄ | " | H | 0 | 78–81 | isopropanol |

-continued

| No. | Ex. | Z | X | R | n | m.p. °C. | recryst. from |
|---|---|---|---|---|---|---|---|
| 31 | 3 | 2,5-F$_2$—C$_6$H$_3$ | " | Cl | 2 | 175–177 | — |
| 32 | 3 | 3-Cl—4-F—C$_6$H$_3$ | " | Cl | 2 | 213–215 | — |
| 33 | 3 | 4-CH$_3$O—C$_6$H$_4$ | " | Cl | 2 | 188–190 | methanol |
| 34 | 2 | phenyl | Pyr. | Cl | 2 | 83–85 | (CH$_2$)$_4$O |
| 35 | 2 | 4-CH$_3$—C$_6$H$_4$ | " | Cl | 2 | 152–154 | CH$_3$CN |
| 36 | 2 | 3-F—C$_6$H$_4$ | " | Cl | 2 | 102–105 | (CH$_2$)$_4$O |
| 37 | 2 | 4-Cl—C$_6$H$_4$ | " | Cl | 2 | 172–175 | — |
| 38 | 2 | 4-Br—C$_6$H$_4$ | " | Cl | 2 | 169–172 | — |

EXAMPLE 6

To the solution of 8.0 g of N-p-fluorophenyl-7-chloro-5-hydroxy-2,3-dihydro-1-benzothiepin-4-carboxamide in 430 ml of chloroform, that of 9.9 g of 87% m-chloroperbenzoic acid in 120 ml of chloroform is added during 10 minutes while stirring at −5°. The reaction mixture is allowed to warm up to room temperature and stirred overnight. The mixture is washed with saturated aqueous sodium bicarbonate, water, saturated aqueous sodium chloride, dried, filtered and evaported. The residue is heated with ethanol and the insoluble material is filtered after cooling to yield the N-p-fluorophenyl-7-chloro-5-hydroxy-2,3-dihydro-1-benzothiepin-1,1-dioxide-4-carboxamide melting at 203°–5°, it is identical in all respects, except for its crystalline form, with the material of Example 3.

The 7-deschloro-analog thereof melts at 182°–184°, it is identical in all respects to the somewhat purer compound No. 27 of Example 5.

Evaporation of the above filtrate and recrystallization from ethanol gives the N-p-fluorophenyl-7-chloro-4-hydroxy-5-oxo-2,3,4,5-tetahydro-1-benzothiepin-1,1-dioxide-4-carboxamide, mp. 175°–7°. The amorphous 7-deschloro-5oxo analog and the N-p-chlorophenyl-4-hydroxy-5-oxo-2,3,4,5-tetrahydro-1-benzothiepin-1,1-dioxide-4-carboxamide, mp 184°–185°, are obtained in a similar manner.

The solution of 1.0 g of N-p-fluorophenyl-7-chloro-5-hydroxy-2,3-dihydro-1-benzothiepin-1,1-dioxide-4-carboxamide in 63 ml of chloroform, when treated with the solution of 0.5 g of 87% m-chloroperbenzoic acid in 5 ml of chloroform in the above manner and the reaction mixture worked up in the same way, affords the N-p-fluorophenyl-7-chloro-4-hydroxy-5-oxo-2,3,4,5-tetrahydro-1-benzothiepin-1,1-dioxide-4-carboxamide, mp. 166°–8° (triturated with ethanol only, instead of recrystallization).

EXAMPLE 7

Preparation of 10,000 tablets each containing 100.0 mg of the active ingredient:

| Formula: | |
|---|---|
| N-p-fluorophenyl-7-chloro-5-pyrrolidino-2,3-dihydro-1-benzothiepin-1,1-dioxide-4-carboxamide | 1,000.00 g |
| Lactose | 2,535.00 g |
| Corn starch | 125.00 g |
| Polyethylene glycol 6,000 | 150.00 g |
| Talcum powder | 150.00 g |
| Magnesium stearate | 40.00 g |
| Purified water | q.s. |

Procedure

All the powders are passed through a screen with openings of 0.6 mm. Then the drug substance, lactose, talcum, magnesium stearate and half of the starch are mixed in a suitable mixer. The other half of the starch is suspended in 65 ml of water and the suspension added to the boiling solution of the polyethylene glycol in 260 ml of water. The paste formed is added to the powders which are granulated, if necessary, with an additional amount of water. The granulate is dried overnight at 35°, broken on a screen with 1.2 mm openings and compressed into tablets using concave punches with 10.3 mm diameter, uppers bisected.

Analogously tablets are prepared, containing one of the other compounds illustrated by the previous or following examples.

EXAMPLE 8

To the solution of 1.0 g of 7-chloro-5-dimethylamino-2,3-dihydro-1-benzothiepin-1,1-dioxide in 3 ml of dry tetrahydrofuran that of 0.51 g of p-fluorophenylisocyanate in 2 ml of tetrahydrofuran is added and the mixture refluxed for 4 hours. It is concentrated, filtered and the residue washed with cold tetrahydrofuran, to yield the N-p-fluorophenyl-7-chloro-5-dimethylamino-2,3-dihydro-1-benzothiepin-1,1-dioxide-4-carboxamide melting at 179°–181°.

The starting material is prepared as follows: To the stirred suspension of 1.09 g of 7-chloro-5-hydroxy-2,3-dihydro-1-benzothiepin-1,1-dioxide in 20 ml of benzene the solution of 0.5 g of titanium tetrachloride in 10 ml of benzene is added dropwise while cooling with ice, and the mixture stirred for ½ hour at 0°. Thereupon the solution of 0.7 g of dimethylamine in 10 ml f benzene is added dropwise and the mixture allowed to warm up to room temperature. It is filtered, the filtrate evaporated, and the residue recrystallized from diethyl ether, to yield the 7-chloro-5-dimethylamino-2,3-dihydro-1-benzothiepin-1,1-dioxide melting at 93°–95°.

EXAMPLE 9

The stirred mixture of 0.3 g of sodium hydride in 20 ml of dry tetrahydrofuran is treated over 1 hour at 0° to −5° with the suspension of 2.1 g of 5-hydroxy-2,3-dihydro-1-benzothiepin-1,1-dioxide in 26 ml of the same solvent. The mixture turns yellow and bubbling occurs after 45 minutes. After the evolution of hydrogen ceases, the mixture is treated in one portion with 3.1 g of p-fluorophenyl-isocyanate dissolved in 7 ml of the same solvent at 0°. It is allowed to come to 25° in about 1 hour, stirred and poured into 50 ml of ice-water and filtered. The filtrate is acidified with concentrated hydrochloric acid, a yellow oil separates, which solidifies on cooling. It is filtered off and recrystallized from ethanol, to yield the N-p-fluorophenyl-5-hydroxy-2,3-dihydro-1-benzothiepin-1,1-dioxide-4-carboxamide melting at 193°–195°; it is identical with compound No. 27 of Example 5.

EXAMPLE 10

The stirred solution of 182 g of 7-chloro-5=pyrrolidino-2,3-dihydro-1-benzothiepin-1,1-dioxide in 180 ml of dry tetrahydrofuran is treated dropwise within 45 minutes, beginning at 20°, with the solution of 115 g of 3,4-dichlorophenylisocyanate in 125 ml of the same solvent. The mixture warms to about 48° during the addition period and is allowed to cool to ambient temperature over night whereupon a solid precipitates. Filtering and washing it with a small amount of tetrahydrofuran and recrystallizing it therefrom affords the N-(3,4-dichlorophenyl)-7-chloro-5-pyrrolidino-2,3-dihydro-1-benzothiepin-1,1-dioxide-4-carboxamide melting at 123°–124°.

EXAMPLE 11

The mixture of 10.0 g N-(3,4-dichlorophenyl)-7-chloro-5-pyrrolidino-2,3-dihydro-1-benzothiepin-1,1-dioxide-4-carboxamide, 100 ml of 95% ethanol and 10 ml of 6N aqueous hydrochloric acid is refluxed for 45 minutes during which a solid precipitates. It is filtered off and washed with a small amount of ethanol, to yield the N-(3,4-dichlorophenyl)-7-chloro-5-hydroxy-2,3-dihydro-1-benzothiepin-1,1-dioxide-4-carboxamide melting at 235°–236°.

The solution of 7.7 g thereof in 70 ml of anhydrous ethanol and 7.5 ml of pyrrolidine is refluxed for 30 minutes, cooled and diluted with diethyl ether until precipitation of the solid ceases. After one hour it is filtered, to yield the corresponding pyrrolidinium salt melting at 195°–197°.

EXAMPLE 12

The stirred solution of 15 g of 7-chloro-5-pyrrolidino-2,3-dihydro-1-benzothiepin-1,1-dioxide in 15 ml of dry tetrahydrofuran is treated within 5 minutes, beginning at 20°, with the solution of 9.4 g of 2,4-dichlorophenylisocyanate in 15 ml of the same solvent. The mixture warms to about 35° during the addition period and after 45 minutes it is heated at 40°–50° for 30 minutes, cooled to 20°, and evaporated. The oily residue is triturated with acetonitrile, to yield the N-(2,4-dichlorophenyl)-7-chloro-5-pyrrolidino-2,3-dihydro-1-benzothiepin-1,1-dioxide-4-carboxamide melting at 148°–151°.

EXAMPLE 13

The mixture of 10.0 g of N-(2,4-dichlorophenyl)-7-chloro-5-pyrrolidino-2,3-dihydro-1-benzothiepin-1,1-dioxide-4-carboxamide, 100 ml of 95% ethanol, and 10 ml of 6N aqueous hydrochloric acid is refluxed for 45 minutes and cooled to 20° whereupon a solid precipitates. It is filtered, the filtrate concentrated to one half its original volume, again filtered and the combined residue washed with ethanol, to yield the N-(2,4-dichlorophenyl)-7-chloro--hydroxy-2,3-dihydro-1-benzothiepin-1,1-dioxide-4-carboxamide melting at 140°–142°.

The solution of 7.1 g thereof in 75 ml of anhydrous ethanol and 7.5 ml of pyrrolidine is refluxed for 30 minutes and a yellow solid precipitates. The mixture is cooled to 20°, mixed with 50 ml of diethyl ether, filtered and washed with such to yield the corresponding pyrrolidinium salt melting at 187°–188°.

EXAMPLE 14

The stirred suspension of 0.4 g of sodium hydride in 6 ml of dimethylformamide is treated dropwise over 25 minutes with the solution of 3.5 g of N-p-fluorophenyl-5-hydroxy-2,3-dihydro-1-benzothiepin-1,1-dioxide-4-carboxamide in 6 ml of the same solvent. After the gas evolution has ceased, 0.68 ml of acetyl chloride in 2 ml of dimethylformamide are added within 10 minutes and stirred at 20° for 1.5 hours. It is poured into a mixture of ice-water and 6 ml of concentrated hydrochloric acid, whereupon the precipitate filtered off and dissolved in 180 ml of methylene chloride. The solution is washed twice with water, dried, evaporated and the residue triturated with methanol, to yield the N-p-fluorophenyl-5-acetoxy-2,3-dihydro-1-benzothiepin-1,1-dioxide-4carboxamide melting at 175°–177°.

EXAMPLE 15

According to the methods illustrated by Examples 10 and 11, the following compounds are prepared from equivalent amounts of the corresponding starting material N-(p-fluoro- or chlorophenyl)-8-chloro-5-pyrrolidino-2,3-dihydro-1-benzothiepin-1,1-dioxide-4-carboxamide, m.p. 148°–149° or 175°–177° respectively, after recrystallization from acotonitrile, and the N-(p-fluoro-or chlorophenyl)-8-chloro-5-hydroxy-2,3-dihydro-1-benzothiepin-1,1-dioxide-4-carboxamide, m.p. 193°–195° or 215°–217° respectively, their pyrrolidinium salts melt at 187°–188° or 197°–198°.

EXAMPLE 16

According to the methods illustrated by the previous examples (indicated in the table below), the following compounds of Formula II are prepared from equivalent amounts of the corresponding reagents: Am=NH-Z, R is in 7-position; Pyr=pyrrolidino,

| No. | Ex. | Z | X | R | n | m.p. °C. | Pyr.-salt m.p. °C. |
|-----|-----|---|---|---|---|----------|-------------------|
| 1 | 10 | 4-F—$C_6H_4$ | Pyr | $CH_3$ | 2 | 148–150A | — |
| 2 | 10 | 4-Cl—$C_6H_4$ | " | " | 2 | 123–125 | — |
| 3 | 10 | 4-F—$C_6H_4$ | " | t . $C_4H_9$ | 2 | 196–198 | — |
| 4 | 10 | " | " | F | 2 | 1560,1580 | $cm^{-1}$ I.R. |
| 5 | 10 | 2-F—$C_6H_4$ | " | Cl | 1 | 214–216 | — |
| 6 | 10 | 2,6-$Cl_2$—$C_6H_3$ | " | " | 2 | 1570,1655 | $cm^{-1}$ I.R. |
| 7 | 11 | 4-F—$C_6H_4$ | OH | $CH_3$ | 2 | 219–220 | 144–145 |
| 8 | 11 | 4-Cl—$C_6H_4$ | " | " | 2 | 222–224 | 173–175 |
| 9 | 11 | 4-F—$C_6H_4$ | " | t . $C_4H_9$ | 2 | 179–182 | 194–196 |
| 10 | 11 | 4-F—$C_6H_4$ | OH | F | 2 | 192–194 | 163–164 |
| 11 | 11 | 2-F—$C_6H_4$ | " | Cl | 1 | — | 186 |
| 12 | 11 | " | " | " | 2 | 141–143 | 194–195 |
| 13 | 11 | 3F—$C_6H_4$ | " | " | 1 | — | 168–169A |
| 14 | 11 | " | " | " | 2 | 187–189 | 197–198 |
| 15 | 11 | 4-Cl—$C_6H_4$ | " | " | 1 | 218–219 | 175–176 |
| 16 | 11 | " | " | " | 2 | 256–257 | 190–191 |
| 17 | 11 | 2,6-$Cl_2$—$C_6H_3$ | " | " | 2 | 126–127B | 175–177 |
| 18 | 11 | 2,4-$F_2$—$C_6H_3$ | " | " | 2 | 201–203 | 173–175 |
| 19 | 11 | 2,5-$F_2$—$C_6H_3$ | " | " | 2 | 175–177 | 194–195 |
| 20 | 11 | 3-$Cl_1$4-F—$C_6H_3$ | " | " | 2 | 213–215 | 159–161 |
| 21 | 11 | 4-$CH_3$—$C_6H_4$ | " | " | 2 | 205–207 | 185–187 |
| 22 | 11 | $C_6H_5$ | " | " | 2 | 173–175 | 204–205 |

-continued

| No. | Ex. | Z | X | R | n | m.p. °C. | Pyr.-salt m.p. °C. |
|---|---|---|---|---|---|---|---|
| 23 | 11 | cyclohexyl | " | " | 2 | 163–166 | 169–170 |
| 24 | 1 | 3-pyridyl | " | " | 2 | 213–214 | 190–191 |
| 25 | 1 | 3-CH₃—2-pyridyl | " | " | 2 | 176–178 | 185–186 |
| 26 | 1 | 5-Cl—2-pyridyl | " | " | 2 | 211–212 | 195–196 |
| 27 | 1 | 2-pyrimidinyl | " | " | 2 | 250d | 188–190 |
| 28 | 1 | 2-pyrazinyl | " | " | 2 | 200–202C | 193–194 |

A = acetonitrile
B = methanol
C = ethylacetate for recrystallization.

EXAMPLE 17

The mixture of 8.0 g of N-(3,4-dichlorophenyl)-7-chloro-5-hydroxy-2,3-dihydro-1-benzothiepin-1,1-dioxide-4-carboxamide in 100 ml of 95% aqueous ethanol is treated in one portion with the solution of 0.7 g of sodium hydroxide in 15 ml of methanol while stirring at room temperature. The mixture is warmed to 50° and allowed to cool to room temperature during 1 hour. It is filtered, the filtrate evaporated and the residue triturated with ethanol diethyl ether (1:9), to yield the corresponding sodium salt monohydrate melting at 225° with decomposition.

Analogously the sodium salt monohydrate of the N-p-fluorophenyl- 7-chloro-5-hydroxy-2,3-dihydro-1-benzothiepin-1,1-dioxide- 4-carboxamide is prepared, melting at 260° with decomposition.

I claim:
1. A 2,3-dihydro-1-benzothiepin-4-carboxylic acid ester, anhydride or halide of the formula

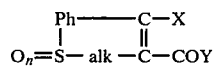

wherein Y is lower alkoxy, alkanoyloxy or halogeno, Ph is 4-chloro-1,2-phenylene, alk is ethylene, X is hydroxy, lower alkanoyloxy, pyrrolidino or piperidino and n is the integer one.

2. A compound as claimed in claim 1 and being the 7-chloro-5-pyrrolidino-2,3-dihydro-1-benzothiepin-1-oxide-carboxylic acid methyl ester.

* * * * *